United States Patent [19]
Lawler

[11] Patent Number: 5,944,521
[45] Date of Patent: Aug. 31, 1999

[54] TOOTH POWDERING APPLICATOR

[75] Inventor: David E. Lawler, Bloomington, Ind.

[73] Assignee: David E. Lawler, P.C., Bloomington, Ind.

[21] Appl. No.: 09/054,131

[22] Filed: Apr. 2, 1998

[51] Int. Cl.⁶ .................................................. A61C 3/02
[52] U.S. Cl. ........................... 433/88; 433/116; 433/216; 433/84; 451/99
[58] Field of Search ............................... 433/88, 116, 83, 433/84, 85, 89, 91, 125, 80, 216; 451/99, 38, 29, 76, 82

[56] References Cited

U.S. PATENT DOCUMENTS

| | | | |
|---|---|---|---|
| 2,814,877 | 12/1957 | Tilden | 433/88 |
| 3,164,153 | 1/1965 | Zorzi | 433/88 |
| 3,971,136 | 7/1976 | Madsen | 433/88 |
| 4,359,317 | 11/1982 | Strohmaier et al. | 433/87 |
| 5,120,219 | 6/1992 | De Farcy | 433/88 |
| 5,203,698 | 4/1993 | Blake et al. | 433/88 |
| 5,312,251 | 5/1994 | Jackson | 433/88 |
| 5,356,292 | 10/1994 | Ho | 433/88 |
| 5,693,313 | 12/1997 | Shiraishi et al. | 424/49 |

*Primary Examiner*—Gene Mancene
*Assistant Examiner*—Philogene Pedro
*Attorney, Agent, or Firm*—Woodard, Emhardt, Naughton Moriarty & McNett

[57] ABSTRACT

A tooth powdering applicator. A container for holding infrared reflective powder has an inlet connected to a source of pressurized fluid and an outlet connected to a rigid outlet tube. A cover is removably threaded on the container to allow for insertion of the powder. The container includes a circuitous path through which the pressurized fluid is directed lifting the powder therein and forcing the powder out through the tube. The tube is rotatably mounted to the container. An optional push button valve is provided to control the flow of fluid.

11 Claims, 2 Drawing Sheets

TOOTH POWDERING APPLICATOR

BACKGROUND OF THE INVENTION

1. Field of the Invention

This invention is in the field of dental tools.

2. Description of the Prior Art

The traditional method of creating a replica tooth is to apply a pliable molding material around the tooth to be replaced with a replica then being created by the cavity formed in the molding material. More recent dental restoration technology utilizes an infrared camera. A white reflective powder comprised of titanium dioxide and talc is applied to the whole tooth creating a uniform color on the tooth and providing a means whereby the infrared camera can photograph and digitize the old tooth. Prior to the powder being sprayed onto the tooth, the dentist prepares the tooth for the porcelain restoration by removing the silver fillings and any lingering decay. A hand held infrared camera is then used to provide an image of the tooth onto a video screen. The replica tooth is then designed through the use of a computer. Once the design of the replica tooth is completed, the dentist utilizes a milling machine for cutting the actual replica tooth from a ceramic block. Such a system is manufactured by Siemens Dental Products Division and distributed in the U.S. by the Patterson Dental Supply Company under the name CEREC 2.

The current technique of applying the reflective powder involves two containers connected together. One container is an aerosol of pressurized butane gas having an outlet directed through a second container of reflective powder which, in turn, has a flexible tube extending therefrom through which the powder is sprayed. Such an applicator is distributed by Vita Zahnfabrik H. Rauter Graph and Co., KG of Bad Sackingen, Germany.

Difficulties are encountered when applying the powder in remote locations of the mouth. The powder needs to be applied evenly. If the powder is too thick on one portion of the tooth then an inaccurate reading by the camera results since the camera reads the top surface of the powder. In many cases, the patient's cheek is in the proximity of the side of the tooth and thus must be forced outwardly therefrom in order for the powder to be sprayed evenly on the side of the tooth. The prior applicator includes an outlet stem which will bend when contacted against the cheek. I have therefore provided a rigid outlet tube to simultaneously force the cheek away from the tooth while powder is being sprayed by the tube onto the tooth. Thus, the dentist may with a single hand move the cheek away from the tooth while spraying the powder. Further, since the tooth has both vertical and horizontal surfaces and surfaces therebetween, the powder must be sprayed at various angles. As a result, the prior art powder applicator requires the dentist to tilt the container of powder in order to properly point the powder outlet towards the tooth surface. Once the powder container is tilted then it is possible for the powder to clump within the container and even clog the outlet. I have therefore designed a powder outlet tube rotatable about its longitudinal axis while allowing the powder container to remain in an upright position. The dentist's hand holding the powder applicator may also be used to rotate the powder outlet tube without necessitating use of the remaining hand of the dentist. The one hand adjustment of the nozzle makes application of powder more precise and more predictable. The powder spray can be directed with complete precision at no risk of clumping or uneven flow.

The powder outlet tube disclosed herein has a right angle bend on the distal end outlet allowing for more easy application of powder in remote areas of the mouth as compared to the prior device having a distal end extending at an angle from the longitudinal axis less than 90°. In an alternate embodiment, I have provided a valve on the powder container allowing the dentist to control the flow with the same hand holding the container allowing for accurate powder application.

I have disclosed my applicator in Disclosure Document No. 423313, filed Aug. 27, 1997 with the U.S. Patent and Trademark Office.

SUMMARY OF THE INVENTION

One embodiment of the present invention is a tooth powdering applicator comprising a container for holding reflective powder to be applied to a tooth to form a reflective coating thereon. The container has a fluid inlet and a powder outlet with a cover movably mounted to the container to allow insertion of powder into the container. A fluid hose has an end connectable to a source of pressurized fluid and another end connected to the container inlet. An outlet tube has an end connected to the powder outlet to receive powder from the container as forced therefrom by fluid introduced into the container from the fluid hose.

It is an object of the present invention to provide a new and improved tool for applying reflective powder to a tooth.

A further object of the present invention is to provide a new and improved dental tool.

A further object of the present invention is to provide a means for evenly applying an infrared reflective power on a tooth.

Related objects and advantages of the present invention will be apparent from the following description.

DESCRIPTION OF THE PREFERRED EMBODIMENT

Figure 1:
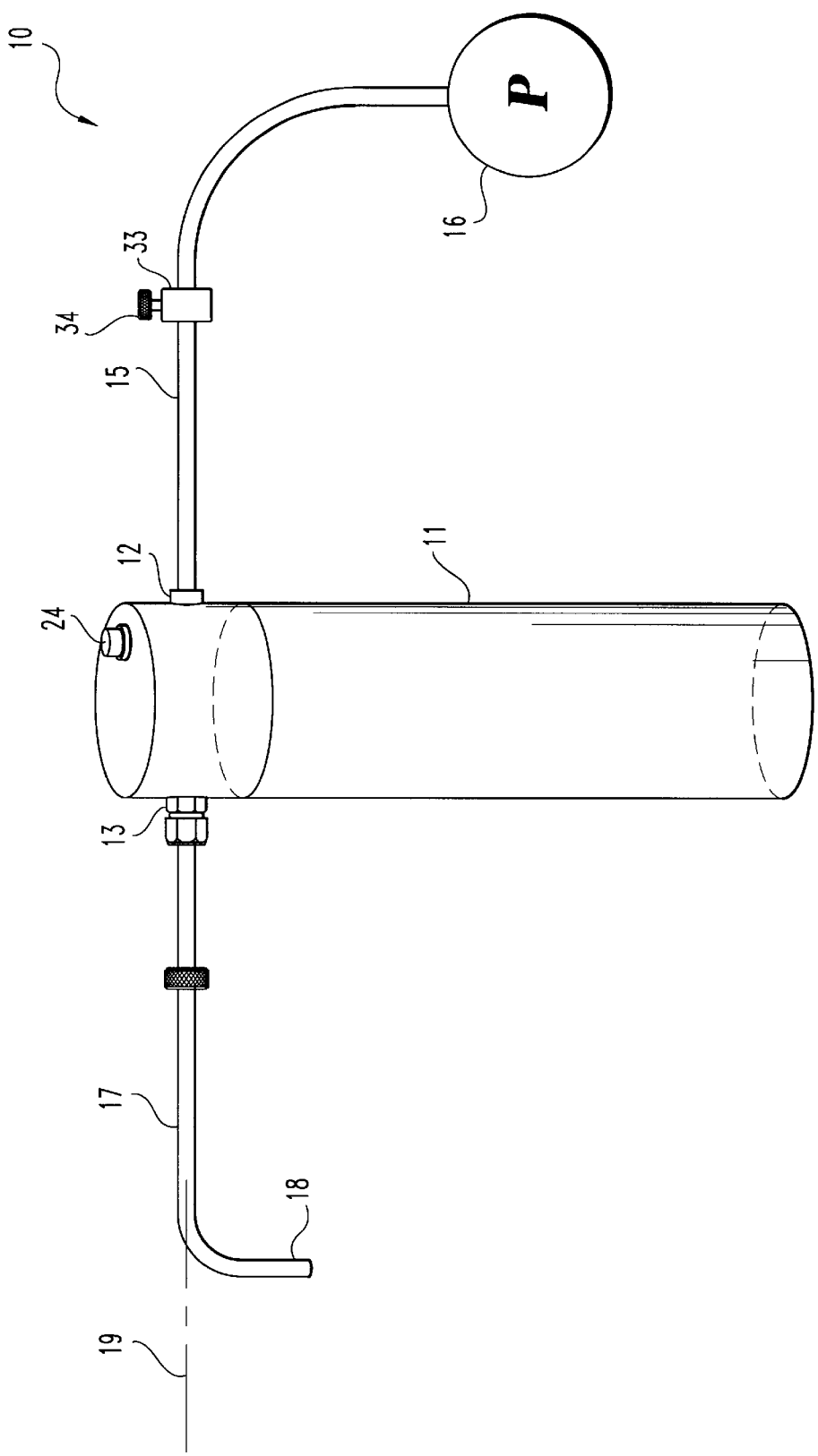
FIG. 1 is a view of the powder applicator incorporating my new invention.
Figure 2:
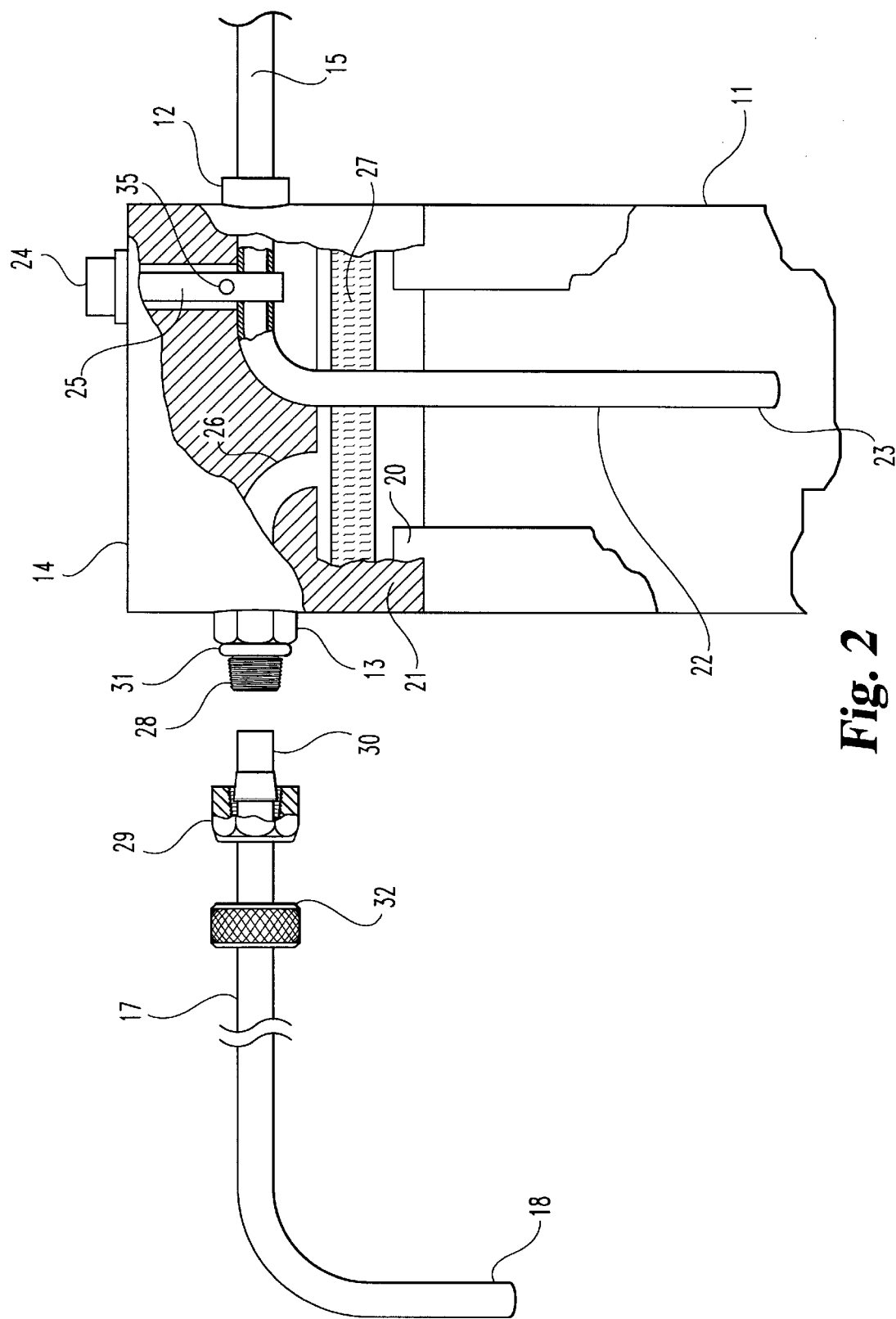
FIG. 2 is an enlarged fragmentary cross-sectional view of the applicator.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

Referring now more particularly to the drawings, there is shown a tooth powdering applicator 10 including a container 11 for holding the reflective powder to be applied to the tooth to form a reflective coating thereon. The container has a fluid inlet 12 and a powder outlet 13 provided in the removable container cover 14. A flexible fluid hose 15 has one end connected to inlet 12 and opposite end connected to a source 16 of pressurized fluid. A rigid metal tube 17 has a proximal end connected to outlet 13 and a distal end 18 through which the powder is sprayed on the tooth. The outlet end 18 is arranged at a 90° angle relative to the longitudinal axis 19 of the tube.

Container 11 is hollow for holding a titanium oxide and talc powder. The top end 20 has a reduced diameter and is externally threaded to meshingly engage with the internally threaded bottom end 21 of cover 14. Thus, cover 14 may be unthreaded from the container to allow for insertion of new powder.

A rigid tube 22 is connected to inlet 12 and has a bottom end 23 extending downwardly into the container. An optional push button valve 24 is mounted to the top of cover 14 and has a member 25 extending downwardly into tube 22. The push button valve and member 25 are spring biased to normally position the member 25 to block flow through tube 22. When the push button is depressed, member 25 moves downwardly aligning passage 35 with tube 22 allowing flow of fluid through the tube. Passage 35 extends through member 25. Other alternative valve structures may be provided in order to control the flow of fluid into the container or the flow of fluid and powder out of the container.

Outlet 13 is connected to an internal passage 26 which opens into the container above an optional mesh screen 27 positioned between the top end 20 of the container and cover 14. The screen extends between the internal threads of the cover thereby filtering the flow of powder out through passage 26 and preventing the powder from clogging passage 26. Source 16 is operable to force pressurized fluid, such as air or inert gas, into the container exiting bottom end 23 of tube 22 thereby stirring the powder within the container and forcing the powder upwardly through screen 27 and out passage 26 to tube 17.

Tube 17 is movably or rotatably mounted to outlet 13 of the applicator. In the embodiment shown in the drawings, outlet 13 includes an externally threaded male connector 28 which threadedly receives an internally threaded female connector 29. Tube 17 has a conically shaped end 30 received in a complimentary sized outlet provided in male connector 28. Tube 17 is rotatable about its longitudinal axis relative to female connector 29. A resilient O-ring 31 extends around male connector 28. Thus, female connector 29 is threadedly mounted onto male connector 28 thereby compressing O-ring 31. Tube 17 is fully rotatably about its longitudinal axis relative to male connector 28 even though connectors 28 and 29 remain stationery. Thus, distal end 18 may be pointed at different angles towards the tooth even though container 11 remains in an upright position.

Disk 32 is fixedly mounted and extends around tube 17 and is rotatably therewith. The circumferential surface of disk 32 provides a finger contact surface allowing the dentist to grasp container 11 with one hand insuring the container remains in an upright position while extending a finger from the same hand onto disk 32 to rotate distal end 18 toward the tooth to be coated. Simultaneously, a finger of the same hand may be used to operate push button valve 24.

Many advantages of the present invention exist over the prior devices. The ability to swivel end 18 while ensuring container 11 is in a stationery or upright position reduces the risk of uneven powder spray. Likewise, screen 27 further limits the uneven powder flow and prevents powder clumping particularly at the inlet of passage 26. The rigid tube 17 may be used to push aside the patient's cheek while the powder is emitted therefrom.

An optional fluid control device 33 may be mounted to hose 15 to control the flow of pressurized fluid through the hose. Hose 15 merely extends through control 33 which has a rotatable stem 34 contactable against the outside surface of the hose to squeeze the hose and restrict the internal diameter thereof. Thus, control 33 may be used as a rough or general control of the pressurized fluid through the hose whereas valve 24 may be used to more finely control the flow of fluid. The tubular shape of container 11 allows the container to be grasped with a single hand with the thumb then being used to depress valve 24 while a finger contacts disk 32 to properly position nozzle outlet 18.

The container includes a circuitous passage consisting of tube 22 extending horizontally from inlet 12 and then vertically downward with the fluid then exiting into the container and flowing back upwardly with the powder entering passage 26. The circuitous passage causes turbulence within the container to stir the powder contained therein.

The removable outlet tube 17 is produced from metal and therefore can be placed in a sterilizer for subsequent use as compared to the prior devices having a plastic outlet tube which must be discarded after a single use.

Many variations are contemplated and included in the present invention. For example, the push button valve 24 is optional and may be used where the source of pressurized fluid has either an on or off position without any variable control provided on the source. The push valve allows the dentist to control the flow of fluid in such instances. On the other hand, the push button valve may not be required if the source of pressurized fluid is provided with a control, such as, a foot valve allowing for variable flow.

What is claimed is:

1. A tooth powdering applicator comprising:
    a container for holding reflective powder to be applied to a tooth to form a reflective coating thereon, said container having a fluid inlet and a powder outlet;
    a cover movably mounted to said container to allow insertion of powder into said container;
    a fluid hose having a source end connectable to a source of pressurized fluid and a container end connected to said inlet;
    a tube having a longitudinal axis and a first end connected to said powder outlet to receive powder from said container as forced therefrom by fluid introduced into said container from said fluid hose and further having a second end through which said powder is sprayed; and,
    a powder screening device mounted in said container between said fluid inlet and said powder outlet to limit uneven powder flow and powder clumping.

2. A tooth powdering applicator comprising:
    a container for holding reflective powder to be applied to a tooth to form a reflective coating thereon, said container having a fluid inlet and a powder outlet;
    a cover movably mounted to said container to allow insertion of powder into said container;
    a fluid hose having a source end connectable to a source of pressurized fluid and container end connected to said inlet;
    a tube having a longitudinal axis and a first end connected to said powder outlet to receive powder from said container as forced therefrom by fluid introduced into said container from said fluid hose and further having a second end through which said powder is sprayed; and,
    means connected to said hose to control flow of fluid into said container; and wherein:
        said means includes a push button operated valve on said container to control flow of said fluid.

3. The applicator of claim 2 wherein:
    said container has a tubular shape with said tube extending outwardly therefrom, said push button operated valve is located atop said container allowing said tubular shape of said container to be grasped by the user's hand and said valve to be operated by the thumb of the same hand while said tube is pointed toward the tooth to be coated with powder.

4. A device for coating a tooth with powder to reflect infrared radiation for infrared photography of the tooth comprising:

a container for holding infrared reflective powder;

a flexible hose connected to said container and connectable to a source of pressurized fluid;

a rigid tube connected to said container and extending outwardly therefrom to hold and spray said powder onto a tooth as forced by pressurized fluid from within said container; and, a control to limit flow of said fluid wherein:

said tube is rotatably mounted to said container and includes a finger contact thereon allowing the user to rotate and point said tube directing powder sprayed therefrom while holding said container in one handed fashion and further comprising, a thumb operated valve mounted to said container allowing control of powder flow therefrom while said container is held in one handed fashion.

5. An infrared reflective powder spraying apparatus for spraying the powder onto a tooth comprising:

holding means for holding infrared reflective powder;

exit means connected to and extending rigidly outwardly from said holding means operable to allow said powder within said holding means to exit therefrom and to be directed onto a tooth, said exit means including a rigid tube movably mounted to said holding means with said tube including a finger contact thereon allowing the user to move said tube relative to said holding means directing powder sprayed therefrom while holding said holding means in one handed fashion;

thumb control means connected to said holding means operable to allow control of powder flow therefrom by a thumb while holding said holding means in one handed fashion; and, pressurized fluid means connected to said holding means for introducing pressurized fluid into said holding means to stir said powder therein and force said powder out said exit means in a spray onto the tooth.

6. The apparatus of claim 5 wherein:

said control means in a push button valve located atop said holding means.

7. The apparatus of claim 6 wherein:

said finger contact includes a disk mounted to said tube with a circumferential surface which forms a finger contact surface.

8. A device for coating a tooth with powder to reflect infrared radiation for infrared photography of the tooth comprising:

a container for holding infrared reflective powder;

a flexible hose connected to said container and connectable to a source of pressurized fluid;

a rigid tube connected to said container and extending outwardly therefrom to hold and spray said powder onto a tooth as forced by pressurized fluid from within said container, said tube is rotatably mounted to said container and includes a finger contact thereon allowing the user to rotate and point said tube directing powder sprayed therefrom while holding said container in one handed fashion; and, a finger operated valve mounted to said container allowing control of powder flow therefrom while said container is held in one handed fashion.

9. A device for coating a tooth with powder to reflect infrared radiation for infrared photography of the tooth comprising:

a container for holding infrared reflective powder;

a flexible hose connected to said container and connectable to a source of pressurized fluid;

a rigid tube connected to said container and extending outwardly therefrom to hold and spray said powder onto a tooth as forced by pressurized fluid from within said container;

a fastener on said container mounting said rigid tube to said container; and wherein:

said tube is rotatably mounted to said container and includes an upraised finger contact thereon allowing the user to rotate and point said tube directing powder sprayed therefrom while holding said container in one handed fashion; and, said tube has a proximal end mounted to said container by said fastener with said proximal end movable relative to said container as said tube is rotated independent of any movement of said fastener.

10. The device of claim 9 wherein:

said upraised finger contact includes a disk fixedly mounted and extending around said tube.

11. The device of claim 9 wherein:

said tube includes a first threaded portion;

said fastener includes a second threaded portion in meshing engagement with said first threaded portion with said first threaded portion and said second threaded portion being stationary while said tube is rotated.

* * * * *